(12) United States Patent
Allen et al.

(10) Patent No.: US 11,101,037 B2
(45) Date of Patent: Aug. 24, 2021

(54) DISAMBIGUATION OF AMBIGUOUS PORTIONS OF CONTENT FOR PROCESSING BY AUTOMATED SYSTEMS

(71) Applicant: International Business Machines Corporation, Armonk, NY (US)

(72) Inventors: Corville O. Allen, Morrisville, NC (US); Timothy A. Bishop, Minneapolis, MN (US)

(73) Assignee: International Business Machines Corporation, Armonk, NY (US)

( * ) Notice: Subject to any disclaimer, the term of this patent is extended or adjusted under 35 U.S.C. 154(b) by 1200 days.

(21) Appl. No.: 15/271,338

(22) Filed: Sep. 21, 2016

(65) Prior Publication Data
US 2018/0082032 A1    Mar. 22, 2018

(51) Int. Cl.
*G16H 50/20*    (2018.01)
*G16H 10/60*    (2018.01)
(Continued)

(52) U.S. Cl.
CPC ........... *G16H 50/20* (2018.01); *G06F 40/289* (2020.01); *G16H 10/60* (2018.01); *G16H 40/20* (2018.01);
(Continued)

(58) Field of Classification Search
CPC ........ G06H 15/20; G16H 50/20; G16H 40/67; G16H 40/20; G16H 40/63; G16H 10/60; G06F 19/00; G06F 40/289
See application file for complete search history.

(56) References Cited

U.S. PATENT DOCUMENTS 27,580,362    9/2012    Brown Eric W et al.
28,629,162    3/2016    Bufe John P et al.
(Continued)

OTHER PUBLICATIONS

Abbas, Assad; Zhang, Limin; Khan, Samee U. A survey on context-aware recommender systems based on computational intelligence techniques. Computing. Archives for Informatics and Numerical Computation; Wien vol. 97, Iss. 7, (Jul. 2015): 667-690.*
(Continued)

*Primary Examiner* — Nathan C Uber
*Assistant Examiner* — Fawaad Haider
(74) *Attorney, Agent, or Firm* — Stephen J. Walder, Jr.; William J. Stock

(57) ABSTRACT

Mechanisms are provided for implementing a disambiguation engine for disambiguating content. Electronic content is received from a corpus of electronic content, and analyzed to identify an ambiguous portion of content. The ambiguous portion of content is a portion of the electronic content whose meaning is not made explicit in the ambiguous portion of content. A context associated with the ambiguous portion of content is determined and a set of one or more context based ambiguous content interpretation rules associated with the determined context is applied to the ambiguous portion of content to generate an interpretation of the ambiguous portion of content. The ambiguous portion of content is annotated based on the interpretation to generate disambiguated electronic content which is stored for processing as part of a subsequent operation.

20 Claims, 5 Drawing Sheets

(51) Int. Cl.
*G06F 40/289* (2020.01)
*G16H 40/67* (2018.01)
*G16H 40/20* (2018.01)
*G16H 40/63* (2018.01)
*G06F 40/40* (2020.01)
*G06F 40/284* (2020.01)
*G06F 40/30* (2020.01)
*G06F 40/35* (2020.01)
*G06F 40/253* (2020.01)
*G06F 16/2457* (2019.01)
*G06F 16/951* (2019.01)
*G06F 16/248* (2019.01)
*G06F 16/9535* (2019.01)

(52) U.S. Cl.
CPC ............ *G16H 40/63* (2018.01); *G16H 40/67* (2018.01); *G06F 16/248* (2019.01); *G06F 16/24575* (2019.01); *G06F 16/24578* (2019.01); *G06F 16/951* (2019.01); *G06F 16/9535* (2019.01); *G06F 40/253* (2020.01); *G06F 40/284* (2020.01); *G06F 40/30* (2020.01); *G06F 40/35* (2020.01); *G06F 40/40* (2020.01)

(56) References Cited

U.S. PATENT DOCUMENTS

| | | | | |
|---|---|---|---|---|
| 9,760,627 | B1* | 9/2017 | Bradley | G06F 16/3344 |
| 2005/0289141 | A1* | 12/2005 | Baluja | G06F 17/2735 |
| 2006/0136270 | A1* | 6/2006 | Morgan | G06F 17/2264 705/3 |
| 2006/0167346 | A1* | 7/2006 | Sarel | A61B 5/0816 600/300 |
| 2008/0235004 | A1* | 9/2008 | Gago | G10L 13/08 704/9 |
| 2009/0216563 | A1* | 8/2009 | Sandoval | G06Q 30/02 705/3 |
| 2009/0287678 | A1 | 11/2009 | Brown et al. | |
| 2011/0066587 | A1 | 3/2011 | Ferrucci et al. | |
| 2011/0119049 | A1 | 5/2011 | Ylonen | |
| 2011/0125734 | A1 | 5/2011 | Duboue et al. | |
| 2013/0007055 | A1 | 1/2013 | Brown et al. | |
| 2013/0018652 | A1 | 1/2013 | Ferrucci et al. | |
| 2013/0066886 | A1 | 3/2013 | Bagchi et al. | |
| 2014/0047375 | A1* | 2/2014 | Koll | G06F 3/0481 715/780 |
| 2014/0142922 | A1 | 5/2014 | Liang et al. | |
| 2014/0279803 | A1* | 9/2014 | Burbank | G06N 5/02 706/47 |
| 2014/0358586 | A1* | 12/2014 | Patel | A61B 34/10 705/3 |
| 2016/0041967 | A1 | 2/2016 | Ghannam et al. | |
| 2016/0117360 | A1 | 4/2016 | Kunc et al. | |

OTHER PUBLICATIONS

"The Era of Cognitive Systems: An inside look at IBM Watson and how it works", IBM Software Group, Whitepaper, IBM Watson Solutions, Sep. 2012, 19 pages.

Al-Harbi, Omar et al., "Lexical Disambiguation in Natural Language Questions (NLQs)", IJCSI International Journal of Computer Science Issues, vol. 8, Issue 4, No. 2, Jul. 2011, pp. 143-150.

Bordes, Antoine et al., "Learning to Disambiguate Natural Language Using World Knowledge", http://www0.cs.ucl.ac.uk/staff/rmartin/grll09/bordes-et-al09.pdf, Dec. 2009, pp. 1-8.

Brill, Eric, "Pattern-Based Disambiguation for Natural Language Processing", Microsoft Research, Proceedings of EMNLP/VLC 2000, Jan. 2000, 8 pages.

Chasin, Rachel, "Word Sense Disambiguation in Clinical Text", Massachusetts Institute of Technology, Jun. 2013, 59 pages.

Demner-Fushman, Dina et al., "What can Natural Language Processing do for Clinical Decision Support?", J Biomed Inform., Oct. 2009, 29 pages.

Ginter, Filip et al., "New Techniques for Disambiguation in Natural Language and Their Application to Biological Text", Journal of Machine Learning Research, vol. 5, Jun. 2004, 17 pages.

High, Rob, "The Era of Cognitive Systems: An Inside Look at IBM Watson and How it Works", IBM Corporation, Redbooks, Dec. 12, 2012, 16 pages.

Josh, Mahesh, "Kernel Methods for Word Sense Disambiguation and Abbreviation Expansion in the Medical Domain", University of Minnesota, Aug. 2006, 127 pages.

McCord, M.C. et al., "Deep parsing in Watson", IBM J. Res. & Dev. vol. 56 No. 3/4 Paper 3, May/Jul. 2012, pp. 3:1-3:15.

McInnes, Bridget T., "Supervised and Knowledge-based Methods for Disambiguating Terms in Biomedical Text using the UMLS and MetaMap", University of Minnesota, Sep. 2009, 249 pages.

Yuan, Michael J., "Watson and healthcare, How natural language processing and semantic search could revolutionize clinical decision support", IBM developerWorks, IBM Corporation, Apr. 12, 2011, 14 pages.

* cited by examiner

DISAMBIGUATION OF AMBIGUOUS PORTIONS OF CONTENT FOR PROCESSING BY AUTOMATED SYSTEMS

BACKGROUND

The present application relates generally to an improved data processing apparatus and method and more specifically to mechanisms for disambiguating ambiguous portions of content so that they may be properly processed by automated systems.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a disambiguation engine for disambiguating content. The disambiguation engine implements the method which comprises receiving, by the data processing system, electronic content from a corpus of electronic content, and analyzing, by ingestion logic of the data processing system, the electronic content to identify an ambiguous portion of content. The ambiguous portion of content is a portion of the electronic content whose meaning is not made explicit in the ambiguous portion of content. The method further comprises determining, by the disambiguation engine of the data processing system, a context associated with the ambiguous portion of content, and applying, by the disambiguation engine, a set of one or more context based ambiguous content interpretation rules associated with the determined context to the ambiguous portion of content to generate an interpretation of the ambiguous portion of content. Moreover, the method comprises annotating, by the disambiguation engine, the ambiguous portion of content based on the interpretation to generate disambiguated electronic content, and storing, by the data processing system, the disambiguated electronic content for processing as part of a subsequent operation.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
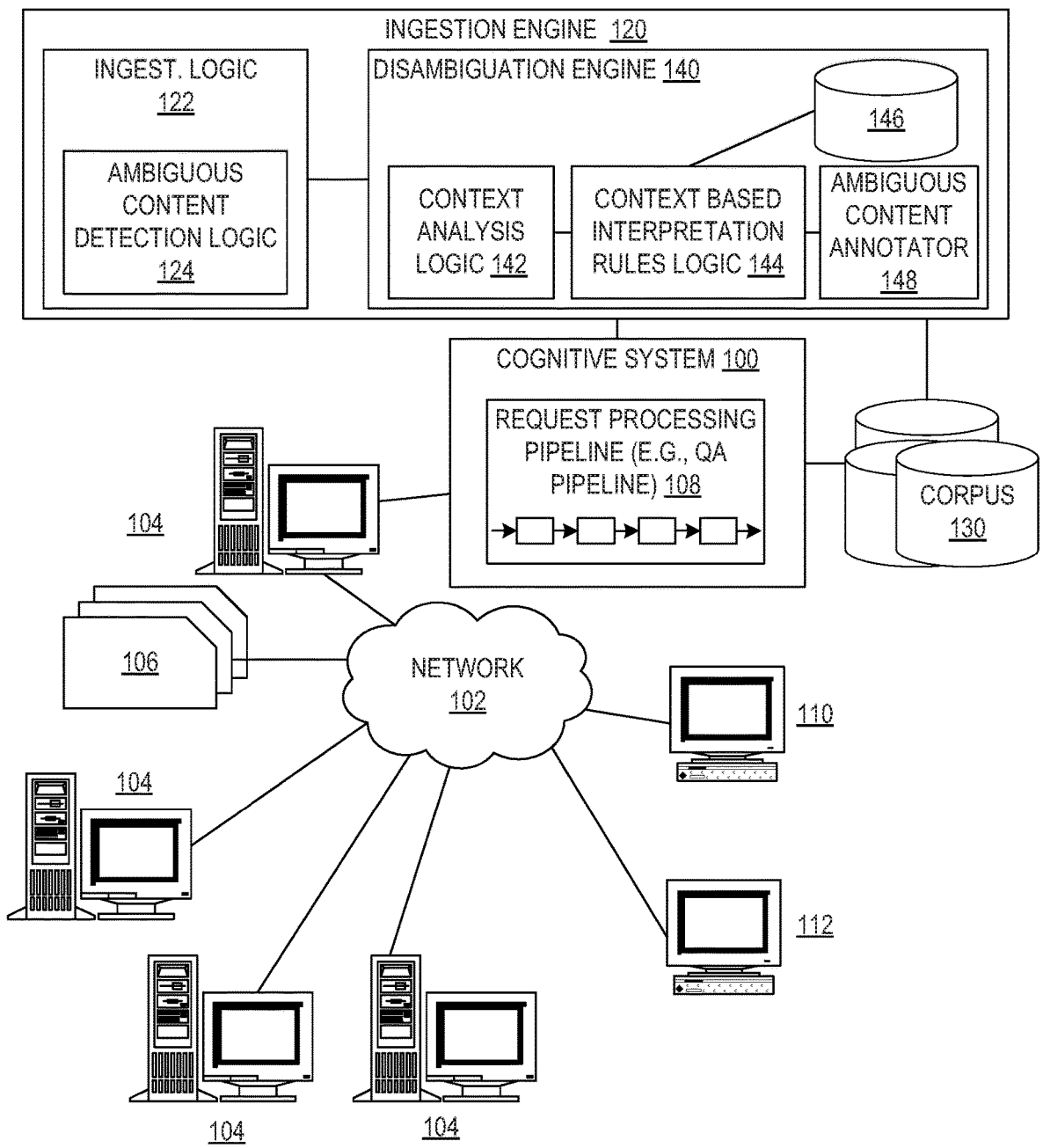
FIG. 1 depicts a schematic diagram of one illustrative embodiment of a cognitive healthcare system in a computer network.

The strengths of current cognitive systems, such as current medical diagnosis, patient health management, patient treatment recommendation systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is the ability to understand ambiguous notations added to natural language content, such as notations added to electronic medical records by medical professionals, for example.

That is, using the medical domain as an example, it is often difficult for automated systems to process notations in electronic medical records (EMRs) when the meaning of such notations is not made explicit in the notation itself. As an example, consider a situation in which a medical professional enters a note into a patient's EMR of the type "10-12" or "2×4". The meaning of these notations is ambiguous since it is not clear from the notation itself what these numerical strings represent. In other words, "10-12" and "2×4" may mean different things in different contexts. In the context of a notation associated with an entry in the patient's EMR documenting a laceration, the numerical string "2×4" may mean that the laceration was 2 centimeters (cm) deep and 4 cm in length. In the context of an entry corresponding to a prescribed medication, the same string "2×4" may mean that the medication is to be taken as "2 pills every 4 hours." A human being reading the EMR may be able to deduce what such ambiguous strings or notations are intended to mean from the context, but an automated system will find it difficult to ascertain what is meant by the notation.

The illustrative embodiments provide mechanisms for disambiguating ambiguous content, such as notations, based on knowledge gathered from other sources of information and an analysis of the context of the ambiguous content. In some illustrative embodiments, these mechanisms process electronic guideline documents (herein references to "documents" are intended to refer to electronic documents or portions of content represented as data structures in a computing environment), such as medical treatment guideline policies, institution operating guidelines, insurance policy guidelines, or any other electronic documentation (collectively referred to herein as "guidelines") specifying a correspondence between context and particular content formats, e.g., notation formats, to thereby generate a dynamic context to use when processing the ambiguous content in a document, such as a patient's EMR.

It should be noted that the present description will use a medical domain as an example for illustrating the inventive aspects of the illustrative embodiments, however the illustrative embodiments are not limited to the medical domain and may in fact operate with any domain of natural language content. Assuming a medical domain, the guidelines are processed to identify key defining characteristics including measurements, ranges, and protocols that are used to define an interpretation context, i.e. a categorization of subject matter with which notations may be associated, e.g., lacerations, cancer treatments, pharmaceuticals, etc. The interpretation context may have associated context based ambiguous content interpretation rules that indicate the way in which particular ambiguous content strings, e.g., ambiguous notations, associated with the interpretation context are to be interpreted, which is referred to herein as the interpretation characteristics of the context based ambiguous content interpretation rule. For example, within the interpretation context of "laceration," a context based ambiguous content interpretation rule may be that a string of the type "A×B", where A and B are numerical values, is interpreted in accordance with the rules interpretation characteristics to mean "a laceration of A cm in depth and B cm in length." Thus, the context based ambiguous content interpretation rules provide rules for mapping formats of notations or ambiguous content to an interpretation of the notations or ambiguous content for the particular context.

Again assuming a medical domain implementation, processors and/or cognitive data processing systems of the illustrative embodiments are enhanced and specifically configured to analyze EMRs, laboratory reports, other medical documents, and the like (or other natural language content depending upon the desired implementation and domain), using the defined interpretation contexts and their associated context based ambiguous content interpretation rules. Thus, for example, when a patient EMR is processed and the processor or cognitive system encounters an ambiguous string in the EMR, the surrounding context of the patient EMR is analyzed to identify key features, e.g., header information, key terms/phrases, etc., indicative of the context which are then mapped to a particular defined context, e.g., the terms "cut" and "bleed" may be indicative of a context of "laceration". The identified most probable context is associated with corresponding context based ambiguous content interpretation rules which define different string patterns and their corresponding interpretation characteristics.

An ambiguous string may be identified as part of a parsing and annotation process of a natural language processing of the content. For example, dictionary based annotators, such as Unified Medical Language System (UMLS) based annotators for example, may be used to assign concept unique identifiers (CUIs) to strings. In some cases, the same string may have multiple annotations, e.g., the string "CT" may be assigned a CUI that represents "Computed Tomography" (such as in a CT scan) and also a CUI that represents "Connecticut" to represent the state. The presence of multiple CUIs is an indication that the meaning of the string is ambiguous. In the case of numerical strings, the numbers typically must have a relationship to some object or measurement, such as "3 pills" where 3 is associated with the noun "pills". Thus, if a numerical string is identified and there is no nearby object, measurement, or the like, with which the numerical string may be paired, then again, the string may be determined to be ambiguous. Various string patterns and rules may be established for defining what is and is not an ambiguous string and these rules may be applied during parsing and annotation, or may applied on results of such parsing and annotation, to identify ambiguous strings in content.

For example, assume that there is a notation in a patient's EMR that is of the type "2×4". When performing parsing and natural language processing of the EMR, this notation is encountered and the system of the illustrative embodiments flags it as an ambiguous portion of content since the system is unable to discern from the notation itself what the notation is referring to, i.e. the parsing and natural language processing mechanisms of the system are unable to correlate the notation to a known type of natural language feature or domain specific entity in a domain specific ontology. In addition, or alternatively, the string pattern may match one or more ambiguous content portion rules criteria or string patterns for indicating an ambiguous term, e.g., multiple possible CUIs, numerical string with no reference to measurement units, numerical string with no reference to an object, etc.

A disambiguation engine of the illustrative embodiments processes the context of the flagged or marked ambiguous portion of content (hereafter referred to as an "ambiguous notation") to identify the context of the ambiguous notation. In order to identify the context, the disambiguation engine may look to the headers of portions of the EMR with which the ambiguous notation is most closely associated, the metadata of the EMR or portion of the EMR in which the ambiguous notation is present, key terms/phrases in surrounding text, e.g., text within a predefined range of the ambiguous notation, any medical codes associated with the surrounding text or the entry in the EMR, and/or the like.

In some cases, other data structures may be accessed as well to obtain additional information for ascertaining the context of the notation. For example, in some illustrative embodiments, medical claims information which may be present in other data structures may be accessed and correlated with the entry in the EMR that is associated with the ambiguous notation. This correlation may be based on timing information indicating a time when medical services were rendered to the patient. This timing information in the medical claims data may be correlated with the date/time specified in the entry in the EMR to identify a correspondence. The corresponding medical claims information may indicate medical codes, billing codes, and/or other text that indicates the context of the entry in the EMR, e.g., what medical condition was being treated by the medical professional and what that treatment ultimately was.

Thus, by analyzing the surrounding content of the ambiguous notation, and also possibly other correlated data structures or sources of information, the disambiguation engine identifies a most probable context for the ambiguous notation. Based on the determined most probable context, a corresponding set of context based ambiguous content interpretation rules associated with the context are evaluated to determine the most probable meaning of the particular ambiguous string in question. This is done by attempting to match the string patterns associated with context based ambiguous content interpretation rules to the ambiguous string so as to identify a matching context based ambiguous content interpretation rule with its corresponding interpretation characteristics indicating the meaning of the matching ambiguous string. For example, in the above scenario, for the context "laceration" there may be a context based ambiguous content interpretation rule specifying the ambiguous notation pattern of "A×B." Having matched a pattern associated with an interpretation context notation processing rule, the ambiguous string is interpreted in light of the associated interpretation characteristics of the matched context based ambiguous content interpretation rule when performing a subsequent operation, such as treatment recommendation operations. Thus, for example, the interpretation characteristics may indicate that the pattern corresponds to A=depth in cm, B=length in cm, and that the natural language equivalent of the notation is "A cm deep and B cm in length."

In some cases, the ambiguous notation may be disambiguated by associating metadata with the ambiguous string that disambiguates the string. For example, in the above example of a notation of "2×4", metadata may be added pointing to the ambiguous string indicating that the notation means "2 cm deep and 4 cm in length." Thus, this metadata may be used by subsequent processing to interpret the string, such as in the case of performing cognitive system based question answering, treatment recommendation for patients, patient diagnosis, or any other cognitive decision support operation.

In some cases, the ambiguous notation may be disambiguated by replacing the notation in the actual document with the disambiguated corresponding interpretation of the notation. Alternatively, rather than replacing the notation, additional natural language content explaining the meaning of the notation may be inserted into the document in association with the ambiguous notation, such as a parenthetical statement, footnote, or other reference portion of text. Any methodology for adding the disambiguated interpretation of the ambiguous notation to the content may be used without departing from the spirit and scope of the present invention.

The disambiguated content may then be stored for further processing to perform a subsequent operation. In some cases, this subsequent operation is a cognitive operation that simulates human thought processes. For example, in a medical treatment recommendation system implementation, the disambiguated content may be used as a basis for determining a medical treatment to recommend for treating a patient based on their historical and current medical conditions, physiological status, laboratory results, and treatments. The treatment recommendation may be presented to a medical professional to assist the medical professional in making decisions about how to best treat the medical condition of the patient.

In other cases, various other types of decision support operations of an analytical, cognitive, or algorithmic nature may be performed using the disambiguated content generated by the mechanisms of the illustrative embodiments. For example, in a law enforcement domain, algorithmic operations may be performed on disambiguated notations in law enforcement personnel reports so as to extract knowledge to assist the law enforcement personnel in the investigation of a crime, e.g., providing recommendations as to questions to ask, recommendations as to people to speak to and items, persons, or events to speak to them about, identifying potential suspects, identifying possible witnesses, etc. Essentially, any cognitive operation, decision support operation, analytical operation, or other algorithmic operation of any suitable domain that is based, at least in part, on the disambiguated content generated by the mechanisms of the illustrative embodiments is intended to be within the spirit and scope of the present invention.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for disambiguating identified ambiguous portions of content in a document, such as in patient electronic medical records (EMRs) in a medical domain, investigator or law enforcement personnel notations in case files or the like in a law enforcement domain, financial analyst notations in a financial domain, or the like. It can be appreciated that the illustrative embodiments are not limited to medical texts and in fact can be applied to notations or ambiguous portions of text present in any natural language content of any of a plethora of different domains. For purposes of the following description, an example medical domain corresponding to operations of a medical treatment recommendation cognitive system will be used as just one example implementation of the illustrative embodiments. Those of ordinary skill in the art, in view of the present description, will be able to discern how the mechanisms of the illustrative embodiments may be applied to other domains without departing from the spirit and scope of the present invention.

In order to configure the disambiguation mechanisms of the illustrative embodiments, the disambiguation mechanisms obtain context based interpretation rules associated with one or more contexts. The configuration may be performed either manually, such as when a subject matter expert (human being) enters the mapping of context to one or more manually defined context based interpretation rules, or through automated mechanisms, such as through ingestion of guideline documents, machine learning based on previous analysis performed on ingested documents, or the like. In some cases, the configuration may be performed in a hybrid manner such that a combination of mechanisms for providing both manually generated and automatically generated context based interpretation rules is utilized.

For example, a subject matter expert (SME) may manually enter a context, e.g. laceration, and may input interpretation characteristics including a format for ambiguous content and the interpretation to be applied to ambiguous content matching the format, e.g., context=laceration, pattern="A×B", interpretation characteristics: A=depth in cm, B=length in cm; interpretation natural language equivalent: "[A] cm deep and [B] cm in length." Alternatively, or in addition, a guidelines document, or other reference document, may be ingested using parsing and natural language processing, or even structural analysis for structured reference documents, to extract similar features of a context based interpretation rule which may be associated with the context specified in the guidelines document or other reference document. For example, parsing and natural language processing may be performed on the guidelines document to extract features from the guidelines document that identify the context, the pattern or format, and the interpretation characteristics which are then compiled into a context based interpretation rule and associated with the context in an entry in configuration data. There may be multiple different contexts and, for each context, there may be one or more context based interpretation rules.

In some cases, as noted above, machine learning may be applied to train the disambiguation logic to recognize certain contexts, associated patterns, and corresponding interpretation characteristics. This machine learning may be performed as an initial configuration operation and/or dynamically as the system operates. In some cases, this machine learning may take user feedback indicating the correctness or incorrectness of an interpretation of an ambiguous portion of content as a way of generating or confirming context based interpretation rules. For example, the system may output to the user that the context of the ambiguous notation is "laceration" and that the pattern "2×4" means "2 pills every 4 hours" and the user may indicate whether that interpretation is correct or not via a user interface. The user may indicate that the interpretation is incorrect and may provide the correct interpretation, e.g., context is "laceration" and the pattern "2×4" means "2 cm deep and 4 cm in length." The system may then update its context based interpretation rules to reflect the correct interpretation by setting the appropriate features of the context based interpretation rule to the correct settings. In this way, the system learns over time the correct way in which to interpret ambiguous portions of content such that the context based interpretation rules may be applied to future instances of ambiguous content.

As noted above, in some illustrative embodiments directed to a medical domain, natural language processing on medical treatment guidelines, health insurance company guidelines, and the like, is performed to identify the context of the guidelines based on the identification of key concepts associated with the guidelines, such as specific medical conditions, specific treatments, patient attributes, lab results, and the like. Corresponding characteristics, such as patterns of text or numerical ranges/values, associated with these concepts, as well as metadata specifying the meaning of the patterns of text or numerical ranges/values, may be identified from the guidelines and associated with the concepts.

For example, a particular health insurance company guideline may specify that the health insurance company will pay X for doctor visits or treatment that is associated with a laceration that is at least Y cm deep and Z cm in length (Y×Z) and retracting in size over a duration of a month. The result of the analysis of the health insurance guidelines is a set of contexts with corresponding key concepts and corresponding context based interpretation rules having patterns and corresponding interpretation characteristics. In performing natural language processing on such a guideline, such key concepts as "laceration," "length," "retracting," "month," and the like may be identified. This information thus, generates a context associated with a laceration. In addition, the key terms/phrases identified via natural language processing further identifies the term "at least", "Y", "Z," and "cm" as indicative of a numerical measure. The key terms "cm", "deep", and "length" indicate the meaning of the terms "Y" and "Z" and specify that "Y" is a measure of depth and "Z" is a measure of length and the units of these measures are "cm". Thus, the characteristics of "Y" and "Z" are associated with the "laceration" context and the meaning metadata of "depth" and "length" and units of "cm" are associated with the characteristics "Y" and "Z," respectively. Thus, a context based interpretation rule is generated in association with the context of "laceration" that includes the pattern "Y×Z" and the interpretation characteristics of "Y cm deep" and "Z cm in length." Moreover, the system may associate a natural language equivalent to the identified pattern as being "Y cm deep and Z cm in length" in the context based interpretation rule as well. This process may be followed for each of the guidelines so as to generate a set of contexts, where each context has a set of context based ambiguous content interpretation rules, each of the context based ambiguous content interpretation rules having associated characteristics and corresponding meaning metadata.

The context and context based interpretation rules are input to the disambiguation logic of the illustrative embodiments to configure the logic to apply these contexts and corresponding context based interpretation rules to ambiguous content found in a document, such as a patient EMR or other medical document, to thereby disambiguate the ambiguous content in the document, e.g., disambiguate an ambiguous notation in the patient EMR. Thus, using the patient EMR as a continuing example, when a patient EMR is processed, such as by way of an ingestion operation or as part of a runtime evaluation of a document for purposes of processing a user request, and the processor encounters an ambiguous string in the patient EMR, the ambiguous string is disambiguated using the mechanisms of the illustrative embodiment. The disambiguated string in the document is then used as a basis for performing additional operations by the processor on the patient EMR, e.g., medical treatment recommendation, diagnosis, etc. More details regarding the way in which ambiguous strings are detected and disambiguated will be provided hereafter with reference to non-limiting illustrative embodiments.

It should be appreciated that the illustrative embodiments may be utilized in many different types of data processing environments. In order to provide a context for the description of the specific elements and functionality of the illustrative embodiments, FIGS. 1-4 are provided hereafter as example environments in which aspects of the illustrative embodiments may be implemented. It should be appreciated that FIGS. 1-4 are only examples and are not intended to assert or imply any limitation with regard to the environments in which aspects or embodiments of the present invention may be implemented. Many modifications to the depicted environments may be made without departing from the spirit and scope of the present invention.

FIGS. 1-4 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing a medical treatment recommendation. It can be appreciated that in order to increase the likelihood that a correct medical treatment recommendation is generated for a patient's medical condition, it is important to be able to understand as much information about the patient's medical history, current medical condition, laboratory test results, and other information included in the patient's electronic medical records. Moreover, it is important to have complete information about current medical treatment guidelines for treating medical conditions of patients. As such, it is important to be able to disambiguate any ambiguous content that may be present in patient electronic medical records (EMRs) as well as medical treatment guidelines. Thus, as described hereafter, the medical treatment recommendation system may be augmented to include the mechanisms of the illustrative embodiments which provide such disambiguation functionality.

It should be appreciated that the healthcare cognitive system 100 in FIG. 1, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?" the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to disambiguating ambiguous portions of content found in documentation ingested by the cognitive system 100. This documentation may be of various types and may be from various sources including medical laboratory reports, insurance claims information, facility admission records, physician office visit and patient treatment documents, or the like. These documents may be separately obtained or may be compiled into one or more patient electronic medical records (EMRs) which are ingested and operated on by the mechanisms of the illustrative embodiments in response to detecting an ambiguous portion of content. The disambiguated documents may then be used as a basis for performing other operations, such as a cognitive operation, analytics operation, decision support operation, or the like. In particular, in the depicted example, the cognitive operation is an operation of the request processing pipeline 108, which may be implemented as a question and answer (QA) pipeline, to generate a medical treatment recommendation for assisting a physician or other medical professional in treating a patient's medical condition.

Thus, since one illustrative embodiment may make use of a cognitive system in which the request processing pipeline is a QA pipeline, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, subsystems, and/or devices other than those that are depicted herein.

The cognitive system 100 is configured to implement a QA pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a disambiguation engine 140 which may be part of an ingestion engine 120 or other logic present in the cognitive system 100. The disambiguation engine 140 may operate in conjunction with any operation of the ingestion engine 120 or cognitive system 100 when parsing and processing the content of a document from the corpus 130 in order to perform a subsequent operation.

The ingestion engine 120, which while shown separate from cognitive system 100 for purposes of illustration may in fact be part of the cognitive system 100 or may be a separate set of logic operating separately on documents in the corpus 130, ingests documents having structured and/or non-structured content and extracts features representative of the content of those documents that are stored as in-memory representations of the documents which may be operated on by the other logic of the cognitive system 100 and/or request processing pipeline 108. This ingestion operation may be performed, for example, as an initial configuration operation for configuring the cognitive system 100 to perform operations for handling requests or answering input questions, for example. Alternatively, such ingestion operations may be performed responsive to the need to ingest a document as determined during runtime operation of the cognitive system 100 when handling a request or generating answers for an input question.

The ingestion logic 122 of the ingestion engine 120 performs known ingestion operations for parsing content of a document, processing the content of the document to extract features representative of the content of the document, and generate an in-memory representation of the content of the document for use by the cognitive system 100 when performing its cognitive operations. Of particular importance to the operation of the illustrative embodiments, the ingestion logic 122 is augmented to implement ambiguous content detection logic 124. The ambiguous content detection logic 124 identifies, as part of the parsing and processing of the content of the document, e.g., natural language processing and feature extraction, portions of the content that are not able to be associated with identifiable features and thus, are ambiguous. This inability to associate the portions of content with identifiable features may be due to the fact that the content itself does not explicitly specify what the portion of content means or represents. For example, an explicit statement of the type "the laceration was 2 cm deep and 4 cm in length (2×4)" explicitly identifies the meaning of the "2×4" portion of the content. However, if the statement were simply "2×4", there is no explicit indication as to what this notation means or how it is to be interpreted, e.g., there are no measurement units associated with the string, there are no references to objects that the string may pertain to, the string may match rules or patterns indicating the string to be ambiguous (such as multiple CUIs associated with the string or the like), etc.

Thus, the ambiguous content detection logic 124 detects the presence of a portion of ambiguous content in an ingested portion of content from the corpus 130. The ambiguous portion of content is flagged (e.g., a metadata ambiguous flag is associated with the portion of content) by the ambiguous content detection logic 124 and identified to the disambiguation engine 140 which operates to disambiguate the flagged ambiguous portion based on an analysis of the context of the ambiguous portion of content.

The disambiguation engine 140 comprises context analysis logic 142 which operates to analyze the text of the surrounding context of the flagged ambiguous portion of content to identify key features in the document indicative of a context. These key features are matched to the concepts associated with the different contexts to thereby identify the most probable context for the ambiguous string. For example, assuming a medical domain implementation, in order to identify the context, the context analysis logic 142 of the disambiguation engine 140 may look to the headers of portions of a patient's electronic medical record (EMR) with which a flagged ambiguous notation is most closely associated, the metadata of the EMR or portion of the EMR in which the ambiguous notation is present, key terms/phrases in surrounding text, e.g., text within a predefined range of the ambiguous notation, any medical codes associated with the surrounding text or the entry in the EMR, and/or the like. As noted above, in some cases, other data structures may be accessed as well to obtain additional information for ascertaining the context of the notation, e.g., medical claims information which may be present in other data structures may be accessed and correlated with the entry in the EMR that is associated with the ambiguous notation.

By analyzing the surrounding content of the ambiguous notation, and also possibly other correlated data structures or sources of information, the context analysis logic 142 of the disambiguation engine 140 identifies a most probable context for the ambiguous notation. For example, string patterns, key terms/phrases, and other features in the various sections of the content may be extracted into data structures which are then analyzed and mapped, via one or more natural language based mapping structures, to corresponding contexts. In some cases, tokens may be extracted from the content and terms from the tokens may be used as a basis for performing a similarity match against a policy which has text, and a pre-configured context for data types and measures, the policy expects. Thus, both a text data structure and repository of context data types of interest may be used to identify the most probable context for the ambiguous notation from the surrounding content.

The identification of the most probable context is provided to the context based interpretation rules logic 144, a corresponding set of context based ambiguous content interpretation rules associated with the context are retrieved from storage 146 and evaluated to determine the most probable meaning of the particular flagged ambiguous portion of content. This is done by attempting to match the string patterns associated with context based ambiguous content interpretation rules to the ambiguous portion of content, e.g., an ambiguous notation string or the like, so as to identify a matching context based ambiguous content interpretation rule with its corresponding interpretation characteristics indicating the meaning of the matching ambiguous portion of content. For example, consider a sentence describing a sore on an appendage which is the right lower leg. This statement may be parsed and analyzed to generate the set of input, for this example, "sore, lower leg" and the pattern would be searched against a policy or rules for the key terms "sore" and "lower leg," as well as their synonyms. An example of a policy could be an insurance policy guideline for lacerations or sores on legs and may match a context that needs the size of the sore. An insurance policy guideline for lacerations or sores that are "high" or "on the arm or hand", on the other hand, may be treated differently, such as requiring a description of the appearance and depth in the context.

Having matched a pattern associated with a context based ambiguous content interpretation rule, the ambiguous portion of content is interpreted in light of the associated interpretation characteristics of the matched context based ambiguous content interpretation rule. That is, the identification of the matching context based ambiguous content interpretation rule is provided to the ambiguous content annotator 148 which uses the interpretation characteristics of the matching rule to generate one or more annotations for the ambiguous portion of content. These annotations may involve associating metadata with the ambiguous portion of content, such that the metadata disambiguates the ambiguous portion of content. In some cases, the ambiguous content annotator 148 may be annotate the ambiguous portion of content by replacing the ambiguous portion of content in the actual document with the disambiguated corresponding interpretation of the ambiguous portion of content. Alternatively, rather than replacing the ambiguous portion of content, additional natural language content explaining the meaning of the ambiguous portion of content may be inserted into the document in association with the ambiguous portion of content, such as a parenthetical statement, footnote, or other reference portion of text pointing to the ambiguous portion of content.

The disambiguated content which has been annotated by the ambiguous content annotator 148 may then be stored in an in-memory representation in memory of the cognitive system 100, or in a more permanent storage in the cognitive system 100 and/or corpus 130, for further processing to perform a subsequent operation. In some cases, this subsequent operation is a cognitive operation performed by the cognitive system 100 that simulates human thought processes. For example, in a medical treatment recommendation system implementation, the disambiguated content may be used as a basis for determining a medical treatment to recommend for treating a patient based on their historical and current medical conditions, physiological status, laboratory results, and treatments. The treatment recommendation may be presented to a medical professional to assist the medical professional in making decisions about how to best treat the medical condition of the patient. In other cases, various other types of decision support operations of an analytical, cognitive, or algorithmic nature may be performed by the cognitive system 100 using the disambiguated content generated by the disambiguation engine 140. The cognitive system 100 may utilize the request processing pipeline 108 to perform such cognitive operations. The pipeline 108 may process the annotations of the disambiguated content as it does other annotations and metadata of the documents in the corpus 130 to thereby perform natural language processing, feature extraction, and other operations as described hereafter, to facilitate responding to a request, answering an input question, or the like.

As noted above, one implementation of the cognitive system 100 and ingestion engine 120 is as part of a medical treatment recommendation system which operates to process a patient's EMR to generate a medical treatment recommendation for treating the patient's medical condition. In such a case, medical professionals may make notations in the patient's EMR that may be ambiguous to automated systems since the notations themselves may not explicitly indicate the meaning of the notation, even though such notations may be readily understandable to human beings. The illustrative embodiments, in such an implementation, may identify such ambiguous notations in the patient EMR and identify key features in the patient EMR within metadata, the surrounding text of the entries in the EMR, etc., which are indicative of the context of the ambiguous notation. Thus, the key features in the patient EMR that are within a close proximity to the encountered ambiguous notation are identified and matched with corresponding concepts in the context mapping entries of the context analysis logic 142 that were used to configure the disambiguation engine 140. The degree of matching between the key features and the concepts for each context may be evaluated and used to rank the contexts relative to one another and select the most probable context of the ambiguous string.

Based on the determined most probable context, a corresponding set of context based ambiguous content interpretation rules are retrieved from storage 146 and evaluated to determine the most probable meaning of the particular notation to thereby identify a matching context based ambiguous content interpretation rule with its corresponding characteristic indicating the meaning of the ambiguous notation. This evaluation may involve matching the ambiguous notation's string pattern to characteristics of the context based ambiguous content interpretation rules and identifying a best match. Thereafter, based on the matching context based ambiguous content interpretation rules, the corresponding interpretation characteristics may be retrieved and used to interpret the ambiguous notation in light of the associated interpretation characteristics of the matched context based ambiguous content interpretation rules. The ambiguous notation may then be annotated and provided to the cognitive system 100 for use in performing cognitive medical treatment recommendation operations In one illustrative embodiment, the source of the context based ambiguous content interpretation rules may be insurance policy information with the cognitive system 100 implementing an insurance claims decision support system.

For example, the mechanisms of the illustrative embodiments may be implemented so as to process an insurance policy to determine whether to approve or reject a claim associated with a procedure or treatment provided to a patient. By first analyzing the policy for that specific procedure or treatment, an interpretation context can be built and defined using the mechanisms of the illustrative embodiments. The interpretation context can then be applied to each clinic note in the patient's EMR when processing notations to deduce whether the procedure should be approved. The interpretation context applies to each notation with the assumptions defined in the context when processing the text. Such mechanisms provide decision support which can expedite the approval of a procedure or treatment under insurance policies.

Figure 2:
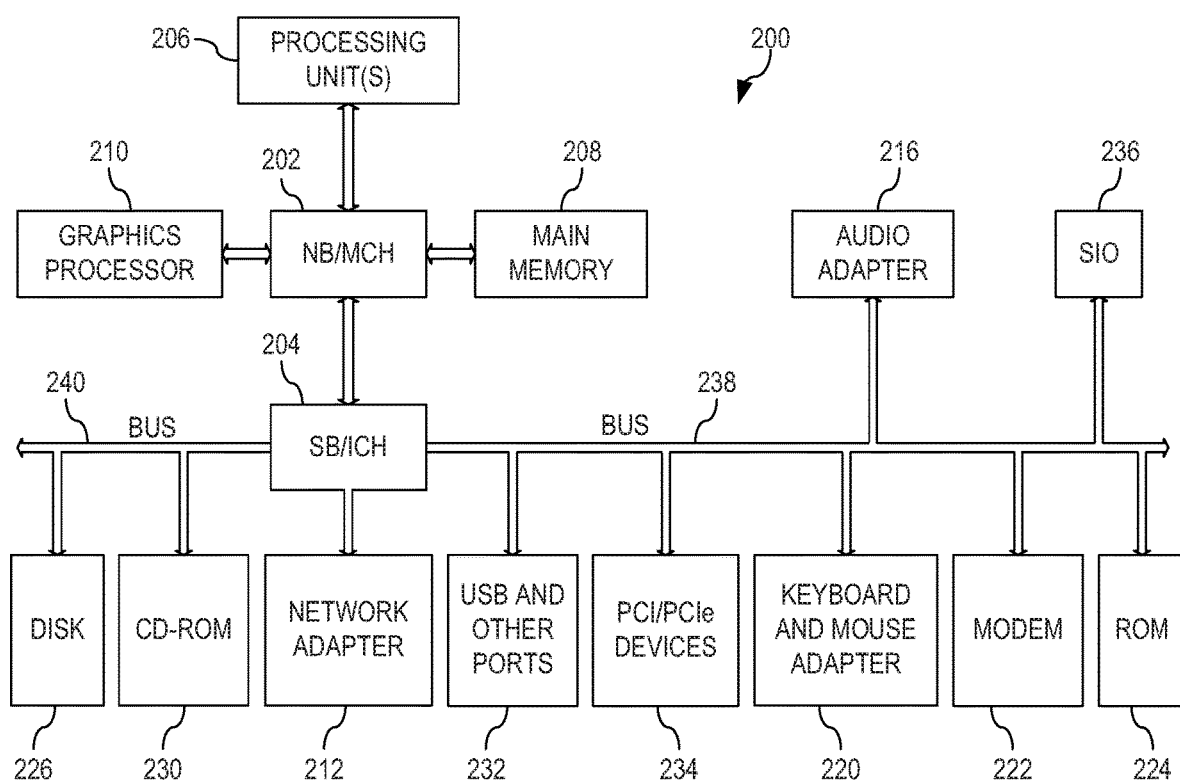
FIG. 2 is a block diagram of an example data processing system in which aspects of the illustrative embodiments are implemented.

As is evident from the above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
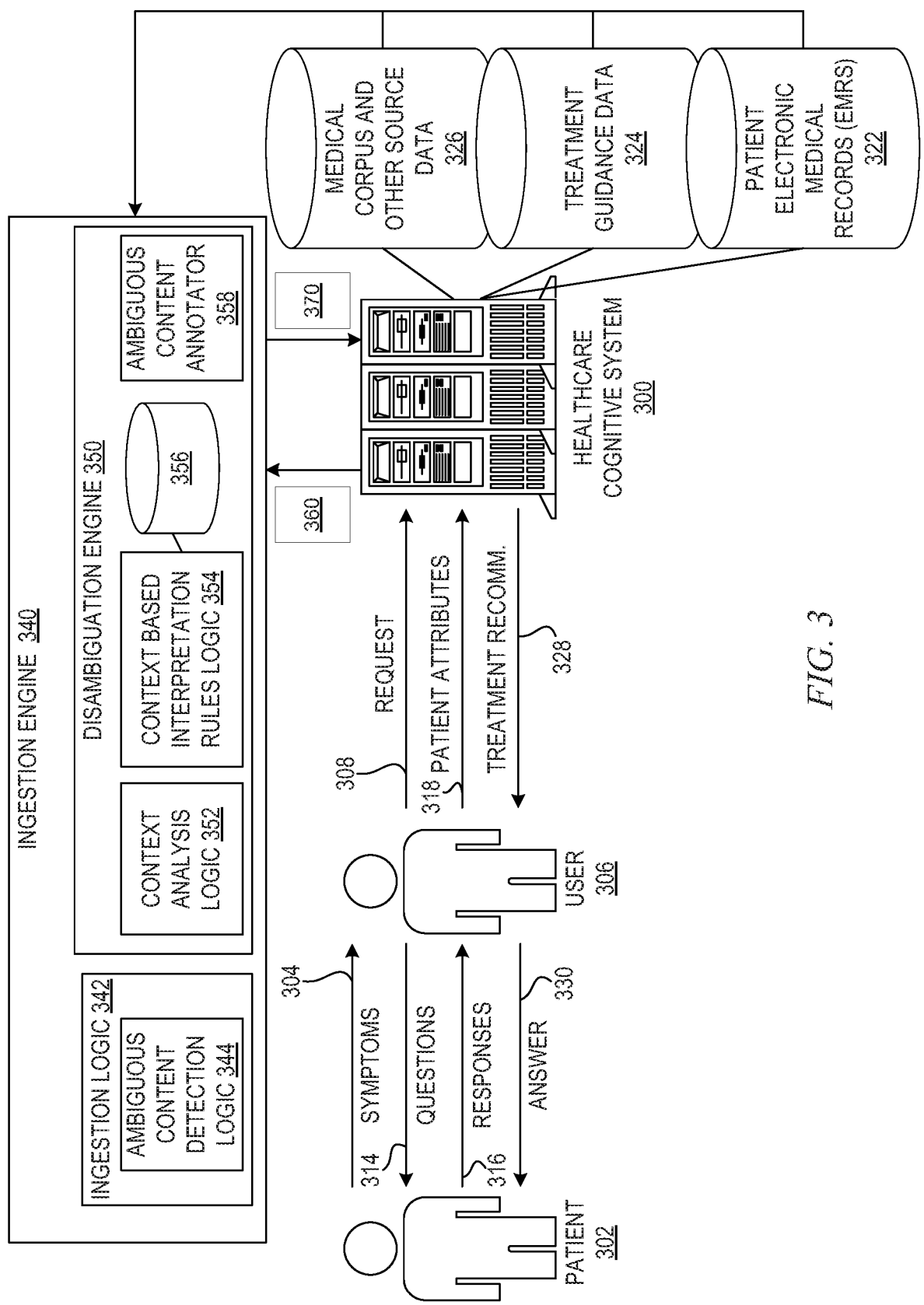
FIG. 3 is an example diagram illustrating an interaction of elements of a healthcare cognitive system in accordance with one illustrative embodiment.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age <=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include an ingestion engine 340 that operates to ingest information from the corpus or corpora 322-326, identify any ambiguous portions of content present in the content of the corpus or corpora 322-326 and disambiguate the ambiguous portions of content based on analysis of the surrounding context. In particular, in one illustrative embodiment, the treatment guidance data 324 and other medical corpus and source data 326 may provide guidelines which may be processed to train the disambiguation engine 350 with regard to contexts and their associated context based ambiguous content interpretation rules, in a manner such as previously described above. The contexts and their associated sets of context based ambiguous content interpretation rules may be stored in the storage 357 of disambiguation engine 350.

In response to a patient 302 interfacing with the user 306, e.g., a doctor or other medical professional, the user may request decision support from the healthcare cognitive system 300, e.g., a request to generate the most appropriate medical treatment for the medical condition of the patient 302. In response, the healthcare cognitive system 300 may analyze the patient EMR 322 for the patient 302 to gather information about the patient 302 which assists in providing the requested decision support.

As discussed previously, many times the patient EMR may have notations or portions of content whose meaning may be ambiguous to the healthcare cognitive system 300 since the meaning is not made explicit in the notation or portion of content itself. As part of an ingestion operation, or in response to a runtime request that initiates processing of a patient EMR 360, these ambiguous notations or portions of content may be identified by the ambiguous content detection logic 344 of the ingestion logic 342. The identified ambiguous content is flagged and provided to the context analysis logic 352 of the disambiguation engine 350 which determines the context surrounding the ambiguous content, e.g., ambiguous notation in the patient EMR 322. For example, if the patient's EMR 360 has a notation of "2×4", this notation is flagged by the ambiguous content detection logic 344 as part of the parsing and natural language processing performed by the ingestion logic 342. The flagged ambiguous notation is identified to the context analysis logic 352 which analyzes the metadata associated with the section of the patient EMR where the ambiguous notation was identified, the key words/phrases in surrounding text, and possibly even correlating the entry in the patient EMR 360 with information from other sources 326, e.g., medical insurance claims information having similar date/time information as the entry in the patient EMR 360, pharmacy prescription fulfillment information, etc.

For example, it may be determined that the notation "2×4" may be associated with an entry that also mentions "Vicodin" which is correlated with a drug name. Moreover, the date/time information for the entry in the patient EMR 360 may be within a few days of an entry in a pharmacy prescription fulfillment database indicating that the patient 302 fulfilled a prescription for "hydrocodone" on the same day as the date/time of the entry in the patient EMR 360. It is further known through the medical corpus and other source data 326 or other knowledge base used by the healthcare cognitive system 300, that "hydrocodone" is a generic form of the drug "Vicodin." Thus, this information together indicates that the ambiguous notation "2×4" is most likely associated with the context of a pharmaceutical.

The identified most probably context of the ambiguous notation "2×4," i.e. a "pharmaceutical" based notation in this running example, is provided to the context based interpretation rules logic 354 which retrieves the context based ambiguous content interpretation rules corresponding to the most probable context from the storage 356. The rules specify a string pattern and the corresponding interpretation characteristics for the string pattern. The string patterns of each of the context based ambiguous content interpretation rules may be compared to the pattern of the ambiguous notation to find a matching context based ambiguous content interpretation rule. If a matching context based ambiguous content interpretation rule is found, the corresponding interpretation characteristics are applied by the ambiguous content annotator 358 to the actual ambiguous notation so as to generate one or more annotations that make explicit the meaning of the ambiguous notation.

For example, a matching context based ambiguous content interpretation rule for the above example may be "A×B" where A=number of pills, B=number of hours, and interpretation string="take [A] pills every [B] hours." The ambiguous content annotator applies these interpretation features to the actual ambiguous notation to generate an annotation specifying the meaning of the ambiguous notation as "take 2 pills every 4 hours." This meaning may be specified in an annotation that is added to metadata pointing to the ambiguous notation, by replacing the ambiguous notation with a disambiguated alternative form, or the like, as previously discussed above. The resulting disambiguated patient EMR 370 may be returned to the healthcare cognitive system 300, stored in an in-memory representation of the patient EMR 370, stored in the patient EMR storage 322, or the like. The healthcare cognitive system 300 may then process the disambiguated patient EMR 370 in a normal manner with the annotations generated by the ambiguous content annotator 358 having made explicit the original ambiguous notations in the original patient EMR 360.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention. It should be appreciated, however, that at no time should the treatment itself be administered to the patient 302 without prior approval of the healthcare professional treating the patient, i.e. final determinations as to treatments given to a patient will always fall on the healthcare professional with the mechanisms of the illustrative embodiments serving only as an advisory tool for the healthcare professional (user 306) and/or patient 302.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
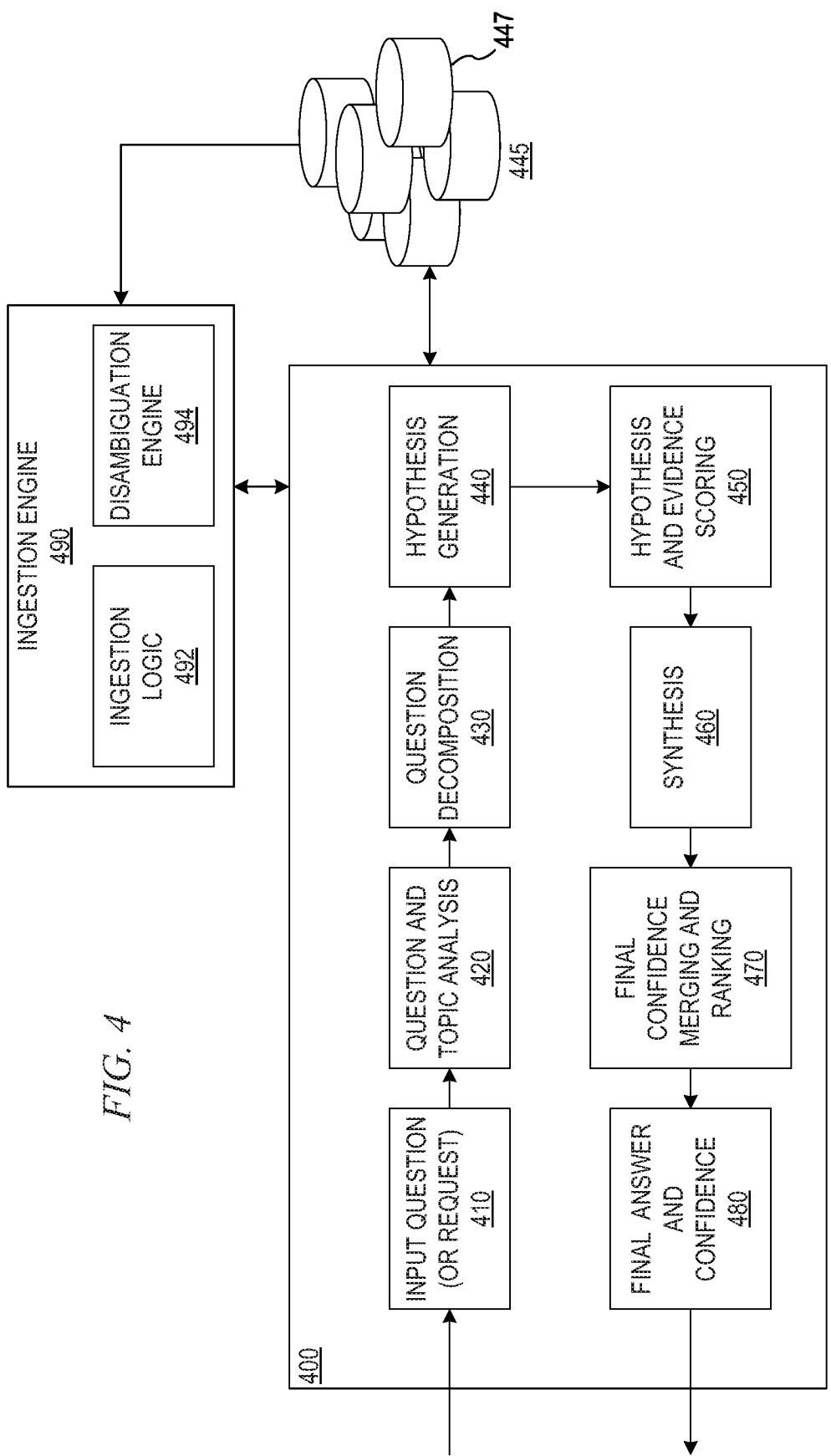
FIG. 4 illustrates a cognitive healthcare system implementing a Question and Answer (QA) or request processing pipeline for processing an input question or request in accordance with one illustrative embodiment.

FIG. 4 illustrates a QA pipeline of a healthcare cognitive system, such as healthcare cognitive system 300 in FIG. 3, or an implementation of cognitive system 100 in FIG. 1, for processing an input question in accordance with one illustrative embodiment. It should be appreciated that the stages of the QA pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

As shown in FIG. 4, the QA pipeline 400 comprises a plurality of stages 410-480 through which the cognitive system operates to analyze an input question and generate a final response. In an initial question input stage 410, the QA pipeline 400 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 400, i.e. the question and topic analysis stage 420, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 4, the identified major features are then used during the question decomposition stage 430 to decompose the question into one or more queries that are applied to the corpora of data/information 445 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 445. That is, these various sources themselves, different collections of sources, and the like, represent a different corpus 447 within the corpora 445. There may be different corpora 447 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 447 within the corpora 445.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 440, to generate hypotheses for answering the input question. These hypotheses are also referred to herein as "candidate answers" for the input question. For any input question, at this stage 440, there may be hundreds of hypotheses or candidate answers generated that may need to be evaluated.

The QA pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 460, the large number of scores generated by the various reasoning algorithms are synthesized into confidence scores or confidence measures for the various hypotheses. This process involves applying weights to the various scores, where the weights have been determined through training of the statistical model employed by the QA pipeline 400 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 400 that identifies a manner by which these scores may be combined to generate a confidence score or measure for the individual hypotheses or candidate answers. This confidence score or measure summarizes the level of confidence that the QA pipeline 400 has about the evidence that the candidate answer is inferred by the input question, i.e. that the candidate answer is the correct answer for the input question.

The resulting confidence scores or measures are processed by a final confidence merging and ranking stage 470 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 480, a final answer and confidence score, or final set of candidate answers and confidence scores, are generated and output to the submitter of the original input question via a graphical user interface or other mechanism for outputting information.

As shown in FIG. 4, in accordance with one illustrative embodiment, the QA pipeline 400 may operate in conjunction with the ingestion engine 490. The ingestion engine 490 provides logic 492 for ingesting documents from the corpus or corpora 445, 447 as discussed previously. As part of this ingestion operation, the ingestion logic 492 may identify ambiguous portions of content in the ingested documents and initiate the operations of the disambiguation engine 494 for disambiguating these ambiguous portions of content. The ingestion engine 490 and its logic may operate in the manner previously described above with regard to one or more of the illustrative embodiments so as to generate annotated content that disambiguates the ambiguous portions of content and makes explicit the meaning of these ambiguous portions in a manner that the QA system pipeline 400 is able to process the ambiguous portions of content and operate on them to perform its functions of hypothesis generation, evidence scoring, and final answer generation.

Figure 5:
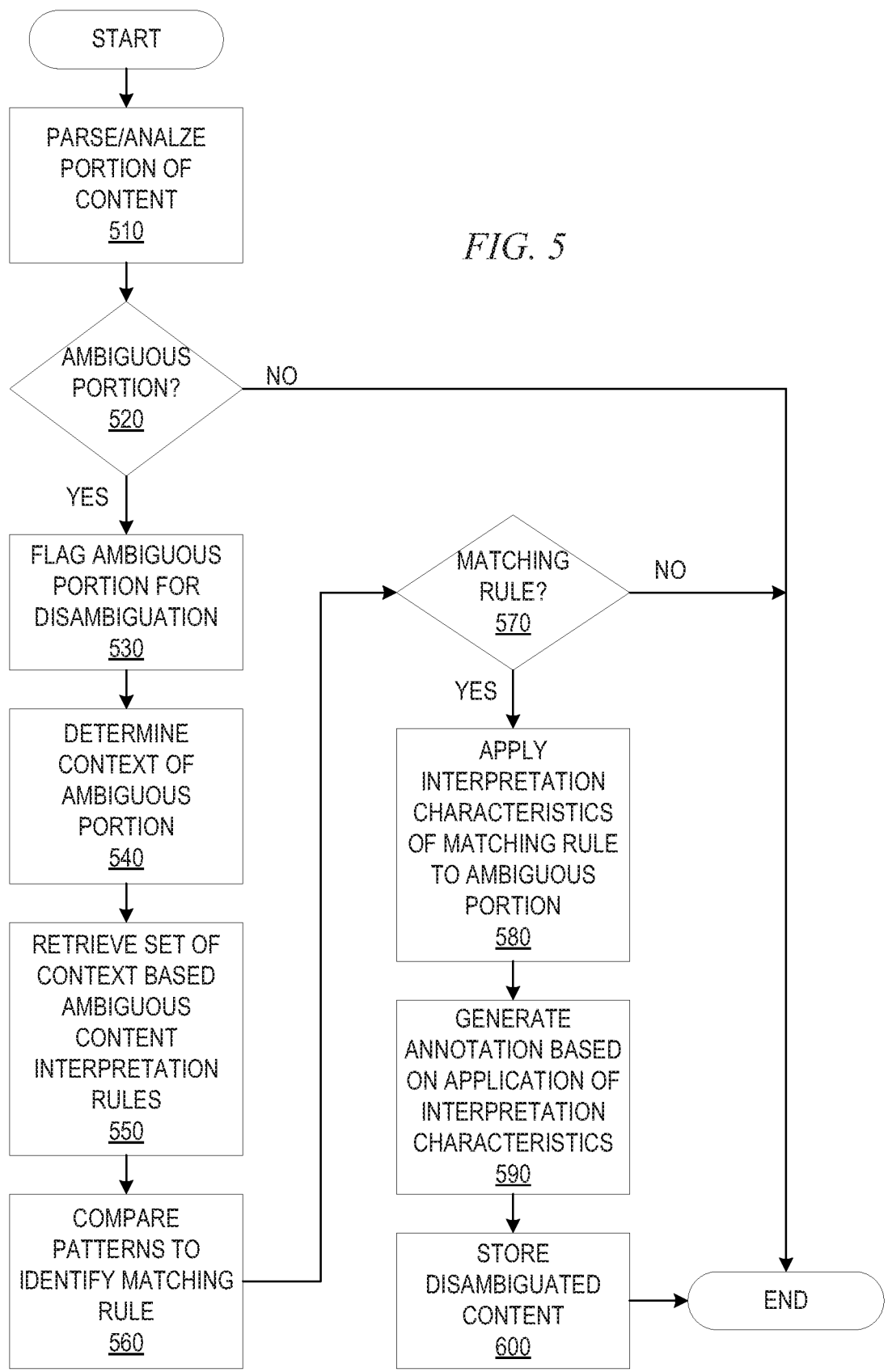
FIG. 5 is a flowchart outlining an example operation for ingesting a portion of content and disambiguating an ambiguous portion of content in accordance with one illustrative embodiment.

FIG. 5 is a flowchart outlining an example operation for ingesting a portion of content and disambiguating an ambiguous portion of content in accordance with one illustrative embodiment. The operation outlined in FIG. 5 may be performed by an ingestion engine, such as ingestion engine 120, 340, or 490, as part of an initial configuration of a cognitive system, in response to a runtime request, or the like.

As shown in FIG. 5, the operation starts with a portion of content being parsed and analyzed using structured/unstructured analysis, such as natural language processing for unstructured content (step 510) (the ingested content is hereafter referred to as a "document" for clarity). A determination is made as to whether an ambiguous portion of content is found in the document (step 520). If not, the operation terminates. If so, the ambiguous portion of content is flagged for disambiguation (step 530). The context of the ambiguous portion of content is determined by analyzing the metadata associated with the ambiguous portion of content, key words/phrases in surrounding text, correlated information from other sources, and the like (step 540). The identified context is correlated with a set of context based ambiguous content interpretation rules (step 550). The string patterns associated with the rules in the set of context based ambiguous content interpretation rules are compared to the string pattern of the ambiguous portion of content to identify a matching rule (step 560). If a matching rule is not found, the operation terminates. If a matching rule is found (step 570), then the interpretation characteristics corresponding to the matching rule are applied to the ambiguous portion of content (step 580). An annotation corresponding to the application of the interpretation characteristics to the ambiguous portion of content is generated and associated with the ambiguous portion of content in the document to thereby generate a disambiguated document (step 590). The disambiguated document is then returned to the cognitive system which performs a cognitive operation based on the disambiguated document (step 600). The operation then terminates.

It should be appreciated that while FIG. 5 assumes that the document only has a single ambiguous portion of content, this is done for simplicity of the description. A document may have multiple ambiguous portions of content and the mechanisms of the illustrative embodiments, such as may perform the operations in steps 510-590 of FIG. 5, will be applied to each such ambiguous portion of content so as to disambiguate each ambiguous portion of content within the document. Moreover, while FIG. 5 assumes a single document being processed for simplicity, it should be appreciated that the outlined operation may be performed for each document ingested such that FIG. 5 is repeated for each such document.

Thus, the illustrative embodiments provide mechanisms for disambiguating identified ambiguous portions of content in documents of a corpus or corpora. The mechanisms of the illustrative embodiments disambiguate these ambiguous portions of content by determining the most probable context surrounding the ambiguous portion and using that most probable context as a mechanism for identifying the string patterns corresponding to the context and their corresponding interpretation characteristics. The mechanisms then provide annotations which disambiguate the ambiguous portions of content such that the meaning of these ambiguous portions is made explicit for use by automated systems, such as a cognitive system.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a disambiguation engine for disambiguating content that implements the method, comprising:
receiving, by the data processing system, electronic content from a corpus of electronic content;
analyzing, by ingestion logic of the data processing system, the electronic content to identify an ambiguous portion of content, wherein the ambiguous portion of content is a portion of the electronic content whose meaning is not made explicit in the ambiguous portion of content;
determining, by the disambiguation engine of the data processing system, a context associated with the ambiguous portion of content at least by analyzing a context portion of content, in the electronic content, associated with the ambiguous portion of content to identify at least one of header information, metadata information, or key term/phrase information associated with the context portion, and mapping the context portion of content to a predefined context having an associated set of one or more context based ambiguous content interpretation rules;
applying, by the disambiguation engine, the set of one or more context based ambiguous content interpretation rules associated with the predetermined context to the ambiguous portion of content to generate an interpretation of the ambiguous portion of content, wherein each context based ambiguous content interpretation rule in the set of one or more context based ambiguous content interpretation rules maps a corresponding text pattern of ambiguous content with an interpretation of the ambiguous content for the predetermined context;
annotating, by the disambiguation engine, the ambiguous portion of content based on the interpretation to generate disambiguated electronic content; and
storing, by the data processing system, the disambiguated electronic content for processing as part of a subsequent operation.

2. The method of claim 1, further comprising:
performing, by the data processing system, a cognitive decision support operation based on the disambiguated electronic content to generate a cognitive decision support output.

3. The method of claim 2, wherein:
the electronic content is a patient electronic medical record corresponding to a patient,
the ambiguous portion of content is a notation generated by a medical practitioner,
the cognitive decision support operation is a treatment recommendation operation executed by a cognitive treatment recommendation system of the data processing system, and the cognitive decision support output is a treatment recommendation for treating a medical condition of the patient.

4. The method of claim 1, wherein analyzing the electronic content to identify the ambiguous portion of content comprises:
applying one or more ambiguous content portion rules or ambiguous content portion string patterns to extracted features of a portion of the electronic content;
determining if the extracted features of the portion of the electronic content satisfy criteria of one of the one or more ambiguous content portion rules or match one of the ambiguous content portion string patterns; and
marking the portion of the electronic content as an ambiguous portion of content in response to the extracted features of the portion of the electronic content satisfying criteria of one of the one or more ambiguous content portion rules or matching one of the ambiguous content portion string patterns.

5. The method of claim 4, wherein the criteria of the one or more ambiguous content portion rules comprise one or more of the extracted features being associated with more than one concept unique identifiers (CUIs), the extracted features comprising a numerical string without reference to a type of measurement or measurement units, or a numerical string without reference to an object.

6. The method of claim 1, wherein determining the context associated with the ambiguous portion of content comprises
correlating the electronic content with other different electronic content from another source that indicates the context for the ambiguous portion of content.

7. The method of claim 1, wherein determining the context associated with the ambiguous portion of content comprises:
correlating the ambiguous portion of content with medical claim information;
correlating at least one medical code in the medical claim information with the ambiguous portion of content; and
identifying the context for the ambiguous portion of content based on the correlated at least one medical code.

8. The method of claim 1, wherein each context based ambiguous content interpretation rule in the set of one or more context based ambiguous content interpretation rules comprises a corresponding string pattern, one or more interpretation characteristics specifying a meaning of at least a portion of the string pattern, and a corresponding natural language interpretation text string specifying an interpretation of the string pattern, wherein annotating the ambiguous portion of content based on the interpretation to generate disambiguated electronic content comprises annotating the ambiguous portion of content based on at least one of the one or more interpretation characteristics or the natural language interpretation text string.

9. The method of claim 8, wherein annotating the ambiguous portion of content based on the interpretation to generate disambiguated electronic content comprises replacing the ambiguous portion of content with a disambiguated equivalent natural language text in the electronic content based on a natural language interpretation text of a matching context based ambiguous content interpretation rule in the set of one or more context based ambiguous content interpretation rules.

10. The method of claim 1, wherein annotating the ambiguous portion of content based on the interpretation to generate disambiguated electronic content comprises storing metadata in association with the electronic content comprising disambiguation information identifying a disambiguated meaning of the ambiguous portion of content.

11. A computer program product comprising a non-transitory computer readable medium having a computer readable program stored therein, wherein the computer readable program, when executed on a computing device, causes the computing device to implement a disambiguation engine which operates to:
receive electronic content from a corpus of electronic content;
analyze the electronic content to identify an ambiguous portion of content, wherein the ambiguous portion of content is a portion of the electronic content whose meaning is not made explicit in the ambiguous portion of content;
determine a context associated with the ambiguous portion of content at least by analyzing a context portion of content, in the electronic content, associated with the ambiguous portion of content to identify at least one of header information, metadata information or key term/phrase information associated with the context portion, and mapping the context portion of content to a predefined context having an associated set of one or more context based ambiguous content interpretation rules;
apply the set of one or more context based ambiguous content interpretation rules associated with the predetermined context to the ambiguous portion of content to generate an interpretation of the ambiguous portion of content, wherein each context based ambiguous content interpretation rule in the set of one or more context based ambiguous content interpretation rules maps a corresponding text pattern of ambiguous content with an interpretation of the ambiguous content for the predetermined context;
annotate the ambiguous portion of content based on the interpretation to generate disambiguated electronic content; and
store the disambiguated electronic content for processing as part of a subsequent operation.

12. The computer program product of claim 11, further comprising:
performing, by the data processing system, a cognitive decision support operation based on the disambiguated electronic content to generate a cognitive decision support output.

13. The computer program product of claim 12, wherein:
the electronic content is a patient electronic medical record corresponding to a patient,
the ambiguous portion of content is a notation generated by a medical practitioner,
the cognitive decision support operation is a treatment recommendation operation executed by a cognitive treatment recommendation system of the data processing system, and
the cognitive decision support output is a treatment recommendation for treating a medical condition of the patient.

14. The computer program product of claim 11, wherein analyzing the electronic content to identify the ambiguous portion of content comprises:
applying one or more ambiguous content portion rules or ambiguous content portion string patterns to extracted features of a portion of the electronic content;
determining if the extracted features of the portion of the electronic content satisfy criteria of one of the one or more ambiguous content portion rules or match one of the ambiguous content portion string patterns; and
marking the portion of the electronic content as an ambiguous portion of content in response to the extracted features of the portion of the electronic content satisfying criteria of one of the one or more ambiguous content portion rules or matching one of the ambiguous content portion string patterns.

15. The computer program product of claim 14, wherein the criteria of the one or more ambiguous content portion rules comprise one or more of the extracted features being associated with more than one concept unique identifiers (CUIs), the extracted features comprising a numerical string without reference to a type of measurement or measurement units, or a numerical string without reference to an object.

16. The computer program product of claim 11, wherein determining the context associated with the ambiguous portion of content comprises
correlating the electronic content with other different electronic content from another source that indicates the context for the ambiguous portion of content.

17. The computer program product of claim 11, wherein determining the context associated with the ambiguous portion of content comprises:
correlating the ambiguous portion of content with medical claim information;
correlating at least one medical code in the medical claim information with the ambiguous portion of content; and
identifying the context for the ambiguous portion of content based on the correlated at least one medical code.

18. The computer program product of claim 11, wherein each context based ambiguous content interpretation rule in the set of one or more context based ambiguous content interpretation rules comprises a corresponding string pattern, one or more interpretation characteristics specifying a meaning of at least a portion of the string pattern, and a corresponding natural language interpretation text string specifying an interpretation of the string pattern, wherein annotating the ambiguous portion of content based on the interpretation to generate disambiguated electronic content comprises annotating the ambiguous portion of content based on at least one of the one or more interpretation characteristics or the natural language interpretation text string.

19. The computer program product of claim 18, wherein annotating the ambiguous portion of content based on the interpretation to generate disambiguated electronic content comprises at least one of:
replacing the ambiguous portion of content with a disambiguated equivalent natural language text in the electronic content based on a natural language interpretation text of a matching context based ambiguous content interpretation rule in the set of one or more context based ambiguous content interpretation rules; or storing metadata in association with the electronic content comprising disambiguation information identifying a disambiguated meaning of the ambiguous portion of content.

20. An apparatus comprising:

a processor; and a memory coupled to the processor, wherein the memory comprises instructions which, when executed by the processor, cause the processor to implement a disambiguation engine which operates to:

receive electronic content from a corpus of electronic content;

analyze the electronic content to identify an ambiguous portion of content, wherein the ambiguous portion of content is a portion of the electronic content whose meaning is not made explicit in the ambiguous portion of content;

determine a context associated with the ambiguous portion of content at least by analyzing a context portion of content, in the electronic content, associated with the ambiguous portion of content to identify at least one of header information, metadata information, or key term/phrase information associated with the context portion, and mapping the context portion of content to a predefined context having an associated set of one or more context based ambiguous content interpretation rules;

apply the set of one or more context based ambiguous content interpretation rules associated with the predetermined context to the ambiguous portion of content to generate an interpretation of the ambiguous portion of content, wherein each context based ambiguous content interpretation rule in the set of one or more context based ambiguous content interpretation rules maps a corresponding text pattern of ambiguous content with an interpretation of the ambiguous content for the predetermined context;

annotate the ambiguous portion of content based on the interpretation to generate disambiguated electronic content; and store the disambiguated electronic content for processing as part of a subsequent operation.

* * * * *